United States Patent
Esch et al.

(10) Patent No.: US 7,261,737 B2
(45) Date of Patent: Aug. 28, 2007

(54) ACCOMMODATING INTRAOCULAR LENS SYSTEM AND METHOD

(75) Inventors: Victor C. Esch, Albuquerque, NM (US); Donald Stenger, Anaheim Hills, CA (US); Barry Cheskin, Mountain View, CA (US)

(73) Assignee: PowerVision, Inc., Belmont, CA (US)

( * ) Notice: Subject to any disclaimer, the term of this patent is extended or adjusted under 35 U.S.C. 154(b) by 181 days.

(21) Appl. No.: 10/971,598

(22) Filed: Oct. 22, 2004

(65) Prior Publication Data

US 2005/0119740 A1 Jun. 2, 2005

Related U.S. Application Data

(63) Continuation-in-part of application No. 10/734,514, filed on Dec. 12, 2003, now Pat. No. 7,122,053.

(60) Provisional application No. 60/433,046, filed on Dec. 12, 2002.

(51) Int. Cl.
*A61F 2/16* (2006.01)

(52) U.S. Cl. .................. 623/6.37; 623/6.13; 623/6.22; 623/6.49

(58) Field of Classification Search ............... 623/6.13, 623/6.22, 6.34, 6.37, 6.43
See application file for complete search history.

(56) References Cited

U.S. PATENT DOCUMENTS

| | | | |
|---|---|---|---|
| 4,253,199 A | 3/1981 | Banko | |
| 4,373,218 A | 2/1983 | Schachar | |
| 4,512,040 A | 4/1985 | McClure | |
| 4,585,457 A | 4/1986 | Kalb | |
| 4,685,921 A | 8/1987 | Peyman | |
| 4,685,922 A | 8/1987 | Peyman | |
| 4,693,717 A | 9/1987 | Michelson | |
| 4,731,078 A | 3/1988 | Stoy et al. | |
| 4,816,031 A | 3/1989 | Pfoff | |
| 4,888,012 A | 12/1989 | Horn et al. | |
| 4,892,543 A | 1/1990 | Turely | |
| 4,902,293 A | 2/1990 | Feaster | |
| 4,932,966 A | 6/1990 | Christie et al. | |
| 4,950,289 A | 8/1990 | Krasner | |
| 4,994,082 A | 2/1991 | Richards et al. | |
| 5,213,579 A | 5/1993 | Yamada et al. | |
| 5,275,623 A | 1/1994 | Sarfarazi | |
| 5,443,506 A | 8/1995 | Garabet | |
| 5,489,302 A | 2/1996 | Skottun | |
| 5,578,081 A | 11/1996 | McDonald | |
| 5,843,188 A | 12/1998 | McDonald | |

(Continued)

FOREIGN PATENT DOCUMENTS

WO WO 2004/010895 2/2004

*Primary Examiner*—Corrine McDermott
*Assistant Examiner*—William H Matthews
(74) *Attorney, Agent, or Firm*—Shay Law Group LLP (57) ABSTRACT

An accommodating intraocular lens is provided having optical parameters that are altered in-situ, wherein an optic portion of the lens includes a lens piston that alters the shape of a lens element of the lens to alter the optical power of the lens, responsive to forces applied to a haptic portion to the lens by contraction of the ciliary muscles. Forces applied to the haptic portion are concentrated by the lens piston to provide a greater dynamic range, and may be further augmented by the use of haptic pistons disposed in the haptic portion of the lens.

27 Claims, 7 Drawing Sheets

U.S. PATENT DOCUMENTS

| | | |
|---|---|---|
| 5,984,962 A | 11/1999 | Anello et al. |
| 6,013,101 A | 1/2000 | Israel |
| 6,117,171 A | 9/2000 | Skottum |
| 6,217,612 B1 | 4/2001 | Woods |
| 6,299,641 B1 | 10/2001 | Woods |
| 6,616,691 B1 | 9/2003 | Tran |
| 6,638,306 B2 | 10/2003 | Cumming |
| 6,645,245 B1 | 11/2003 | Preussner |
| 6,660,035 B1 | 12/2003 | Lang et al. |
| 6,692,525 B2 | 2/2004 | Brady et al. |
| 6,695,881 B2 | 2/2004 | Peng et al. |
| 6,712,848 B1 | 3/2004 | Wolf et al. |
| 6,730,123 B1 | 5/2004 | Klopotek |
| 2001/0016771 A1 | 8/2001 | Cumming |
| 2003/0050695 A1 | 3/2003 | Lin et al. |
| 2003/0149480 A1 | 8/2003 | Shadduck |
| 2004/0006387 A1 | 1/2004 | Kelman |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0082994 A1 | 4/2004 | Woods et al. |
| 2004/0085511 A1 | 5/2004 | Uno et al. |
| 2004/0111151 A1 | 6/2004 | Paul et al. |
| 2004/0111152 A1 | 6/2004 | Kelman |
| 2004/0127984 A1 | 7/2004 | Paul et al. |
| 2004/0162612 A1 | 8/2004 | Portney et al. |
| 2004/0181279 A1 | 9/2004 | Nun |
| 2006/0041307 A1* | 2/2006 | Esch et al. .................. 623/6.13 |

* cited by examiner

ACCOMMODATING INTRAOCULAR LENS SYSTEM AND METHOD

REFERENCE TO RELATED APPLICATIONS

This application is a continuation-in-part of U.S. patent application Ser. No. 10/734,514, filed Dec. 12, 2003, now issued as U.S. Pat. No. 7,122,053, and claims the benefit of priority from U.S. provisional patent application Ser. No. 60/433,046, filed Dec. 12, 2002.

FIELD OF THE INVENTION

The present invention relates to intraocular lenses ("IOLs") having optical parameters that are changeable in-situ. More particularly, the invention has applications in IOLs for in-capsule implantation for cataract patients, wherein forces applied by the ciliary muscles in the eye induce movement of fluid media within the interior of the IOL, thereby altering an optical power of the lens to provide accommodation.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule supported by the ciliary muscles, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein), move between a relaxed state (corresponding to the moderately convex shape) to a contracted state (corresponding to the highly convex shape). Because the lens itself is composed of viscous, gelatinous transparent fibers, arranged in an "onion-like" layered structure, forces applied to the capsule by the ciliary muscles cause the lens to change shape.

Isolated from the eye, the relaxed capsule and lens take on a spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter-muscular mode. Accordingly, when the ciliary muscles are relaxed, the capsule and lens are pulled about the circumference to a larger diameter, thereby flattening the lens, whereas when the ciliary muscles are contracted the lens and capsule relax somewhat and assume a smaller diameter that approaches a more spherical shape. This mechanism, called the "ciliary process" increases the diopter power of the lens.

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition known as "presbyopia". Because the imaging distance is fixed, presbyopia typically entails the need for bi-focals to facilitate near and far vision.

Apart from age-related loss of accommodation ability, such loss is innate to the placement of IOLs for the treatment of cataracts. IOLs are generally single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability.

Although previously known workers in the field of accommodating IOLs have made some progress, the relative complexity of the methods and apparatus developed to date have prevented widespread commercialization of such devices. Previously known these devices have proved too complex to be practical to construct or have achieved only limited success, due to the inability to provide accommodation of more than 1-2 diopters.

U.S. Pat. No. 5,443,506 to Garabet describes an accommodating fluid-filled lens wherein electrical potentials generated by contraction of the ciliary muscles cause changes in the index of refraction of fluid carried within a central optic portion. U.S. Pat. No. 4,816,031 to Pfoff discloses an IOL with a hard PMMA lens separated by a single chamber from a flexible thin lens layer that uses microfluid pumps to vary a volume of fluid between the PMMA lens portion and the thin layer portion and provide accommodation. U.S. Pat. No. 4,932,966 to Christie et al. discloses an intraocular lens comprising a thin flexible layer sealed along its periphery to a support layer, wherein forces applied to fluid reservoirs in the haptics vary a volume of fluid between the layers to provide accommodation.

Although fluid-actuated mechanisms such as described in the aforementioned patents have been investigated, accommodating lenses currently nearing commercialization, such as developed by Eyeonics, Inc. (formerly C&C Vision, Inc.) of Aliso Viejo, Calif., rely on ciliary muscle contraction of the IOL haptics to move the optic towards or away from the retina to adjust the focus of the device.

In view of the foregoing, it would be desirable to provide apparatus and methods that restore appropriate optical focusing power action to the human eye.

It further would be desirable to provide methods and apparatus wherein a dynamic lens surface may be effectively manipulated by the ciliary muscular mechanisms within the eye.

It still further would be desirable to provide methods and apparatus that utilize pressure applied by the accommodating muscular action to obtain a volumetric mechanical advantage in deflecting an optical surface of the IOL. In particular, it would be desirable to provide an IOL in which muscular pressure may be applied through one or more actuators to obtain such volumetric mechanical advantage.

SUMMARY OF THE INVENTION

In view of the foregoing, it is an object of the present invention to provide apparatus and methods that restore appropriate optical focusing power action to the human eye.

It is a further object of this invention to provide methods and apparatus wherein a dynamic lens surface may be effectively manipulated by the ciliary muscular mechanisms within the eye.

It is another object of the present invention to provide methods and apparatus that utilize pressure applied by the accommodating muscular action to obtain volumetric mechanical advantage in deflecting an optical surface of the IOL.

It is a further object of this invention to provide methods and apparatus for reversibly applying muscular pressure, through one or more actuators, to obtain a volumetric mechanical advantage in altering the optical parameters of one of more surfaces of the IOL.

These and other objects of the present invention are accomplished by providing an intraocular lens responsive to variations in capsule shape and/or forces exerted by the ciliary muscle to actuate one or more transducers. The transducers are coupled to a lens piston that deflects a surface of the lens, e.g., from a moderately convex to a highly convex shape. In accordance with the principles of the present invention, the lens piston provides a significant volumetric mechanical advantage in effecting deflection of an anterior or posterior surface of the lens, and greater dynamic range, compared to previously-known fluid-mediated accommodation systems.

In the context of the present invention, "volumetric mechanical advantage" means that a motion of the ciliary muscle, e.g., 100 microns, is amplified by the ratio of the transducer area over which force is applied to the area of the lens piston. It is expected that ratios of two or more may be achieved, but a ratio of one also is expected to be adequate for most patient populations. Operation of the lens piston may be enhanced using one or more haptic pistons that provide a further volumetric mechanical advantage compared to previously-known fluid-mediated accommodation systems.

In a preferred embodiment, the intraocular lens comprises an optic portion and a haptic (or non-optic) portion. The optic portion comprises a light transmissive substrate defining one or more fluid channels, one or more lens pistons coupled in fluid communication with the fluid channels, and anterior and posterior lens elements. One of the anterior and posterior lens elements includes a deflectable surface that is operatively coupled to the one or more lens pistons so that movement of the lens pistons causes the anterior or posterior lens to deflect. The other of the anterior or posterior lens elements may be coupled to the substrate or integrally formed therewith.

The haptic portion is disposed at the periphery of the optic portion and may comprise one or more arms that extend outward from the optic portion, each arm including a fluid channel coupled in fluid communication with the fluid channels in the optic portion. The haptic portion includes one or more transducers that engage the interior of the capsule and/or ciliary muscle, so that action of the ciliary process is communicated via the fluid channels to the one or more lens pistons. More preferably, the transducers further comprise a haptic piston including a force-concentrating element operatively coupled to a diaphragm.

In accordance with one aspect of the present invention, the transducer may be biased to maintain the lens piston in an accommodated state. For such embodiments, relaxation of the ciliary muscle causes the zonules to transition the capsule to an ellipsoidal shape. The capsule thereby applies compressive forces that deform the transducer, reduce fluid pressure in the lens piston, and cause the lens to transition to the unaccommodated state. Alternatively, the lens piston may not be pressurized when the transducer is in the undeformed state. In this latter case, the lens may be configured so that contraction of the ciliary muscle induces thickening near the capsular equator, which in turn compresses the transducer to pressurize the lens piston and transition the lens to the accommodated state.

The haptic pistons, lens piston(s) and fluid volumes may be manufactured so as to provide predetermined actuation forces appropriate for predetermined populations of patients, or alternatively may be tailored on a patient-by-patient basis, thereby enhancing the ability of the intraocular lens to adjust to different optical focusing powers and force magnifications.

In addition, the haptic portion may include one or more features, such as flanges, that apply a force on the capsular bag to maintain tension on the zonules. This arrangement enables the transducer to follow the equator of the capsule.

Methods of making and using the lens of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

In accordance with the principles of the present invention, an intraocular lens is provided having a haptic portion and a light-transmissive optic portion. The optic portion contains one or more fluid-mediated pistons arranged to apply a deflecting force on an anterior or posterior element of the lens to provide accommodation of the lens. As used herein, the lens is fully "accommodated" when it assumes its most highly convex shape, and fully "unaccommodated" when it assumes its most flattened, ellipsoidal state. The lens of the present invention is capable of dynamically assuming any desired degree of accommodation between the fully accommodated state and fully unaccommodated state responsive to the ciliary process.

Forces applied to a transducer disposed in the haptic portion by the ciliary process are communicated to one or more lens pistons that control deflection of an anterior or posterior element of the lens, resulting in a larger dynamic range of accommodation than heretofore is believed to have been available. The lens piston and surrounding fluids all are index-matched to prevent the occurrence of optical aberrations throughout the range of motion of the lens piston.

In accordance with another aspect of the present invention, the transducer may include one or more haptic pistons that provide a volumetric mechanical advantage with respect to forces applied by the ciliary process to the lens piston.

Figure 1:
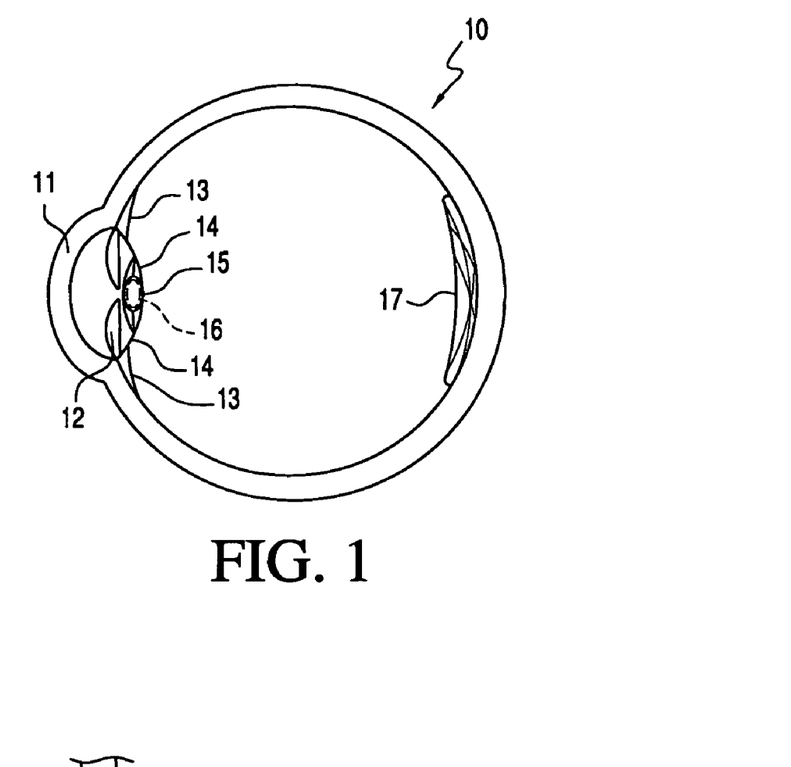
FIG. 1 is a sectional side view of a human eye.
Figure 2A:
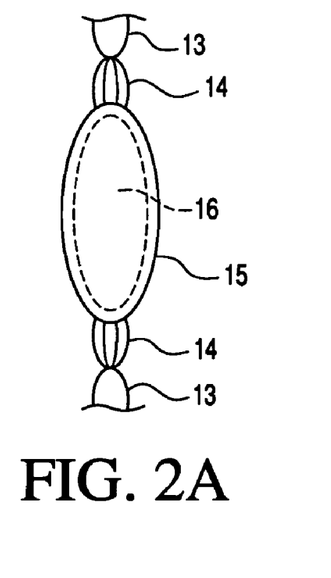
FIGS. 2A and 2B are, respectively, sectional side views of the lens and supporting structures of FIG. 1 illustrating relaxed and contracted states of the ciliary muscles.
Figure 2B:
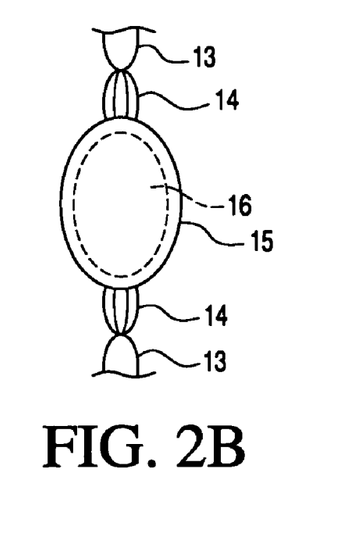

Referring to FIGS. 1 and 2, the structure and operation of a human eye are first described as context for the present invention. Eye 10 includes cornea 11, iris 12, ciliary muscles 13, ligament fibers or zonules 14, capsule 15, lens 16 and retina 17. Natural lens 16 is composed of viscous, gelatinous transparent fibers, arranged in an "onion-like" layered structure, and is disposed in transparent elastic capsule 15. Capsule 15 is joined by zonules 14 around its circumference to ciliary muscles 13, which are in turn attached to the inner surface of eye 10. Vitreous 18 is a thick, transparent substance that fills the center of eye 10.

Isolated from the eye, the relaxed capsule and lens takes on a spherical shape. However, when suspended within the eye by zonules 14, capsule 15 moves between a moderately convex shape (when the ciliary muscles are relaxed) to a highly convex shape (when the ciliary muscles are contracted). As depicted in FIG. 2A, when ciliary muscles 13 relax, capsule 15 and lens 16 are pulled about the circumference, thereby flattening the lens. As depicted in FIG. 2B, when ciliary muscles 13 contract, capsule 15 and lens 16 relax and become thicker. This allows the lens and capsule to assume a more spherical shape, thus increasing the diopter power of the lens.

Accommodating lenses currently nearing commercialization, such as the Crystalens device under development by Eyeonics, Inc., Aliso Viejo, Calif., typically involve converting diametral movements of the ciliary muscle into forward and backward movement of an optic portion of the IOL relative to the retina. This approach is thought to be required because, following extraction of a cataract-effected lens, the capsule is very loose, and the zonules that couple the capsule to the ciliary muscles are no longer in tension. Devices such as the Crystalens thus do not employ the natural accommodation mechanisms described above, but instead rely directly on radially inward compressive forces applied by the ciliary muscle to the haptics of the IOL.

By contrast, according to one aspect of the present invention, an intraocular lens is designed to engage capsule 15 and to transition between the accommodated and unaccommodated states responsive to forces applied to capsule 15 by ciliary muscle 13 and zonules 14, thereby more closely mimicking operation of the natural eye. Alternatively, the haptic portion may be disposed directly in contact with the ciliary muscle.

Figure 3A:
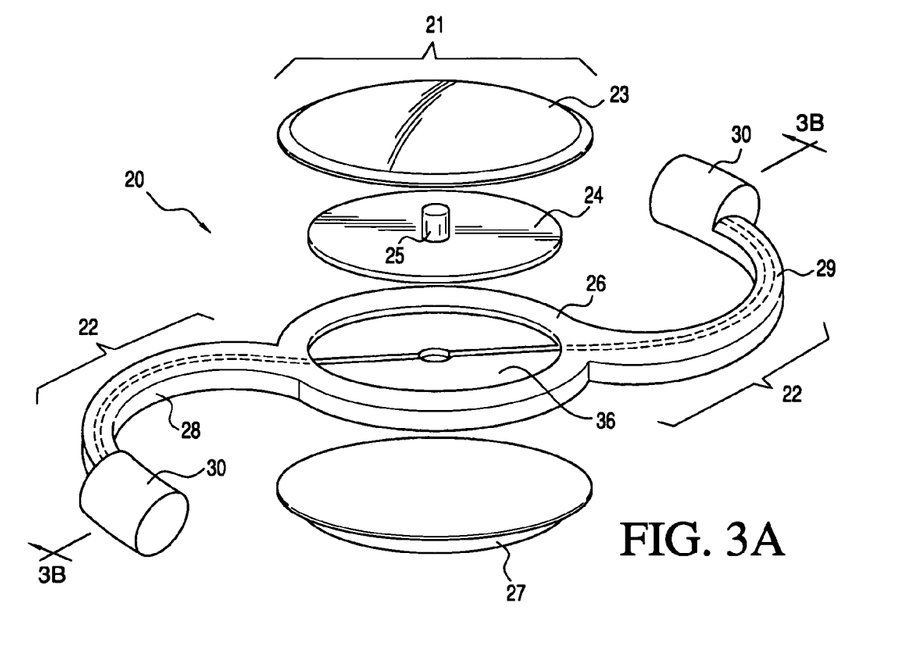
FIGS. 3A and 3B are, respectively, an exploded perspective view and side sectional view, taken along line 3B-3B of FIG. 3A, of an exemplary intraocular lens of the present invention.
Figure 3B:
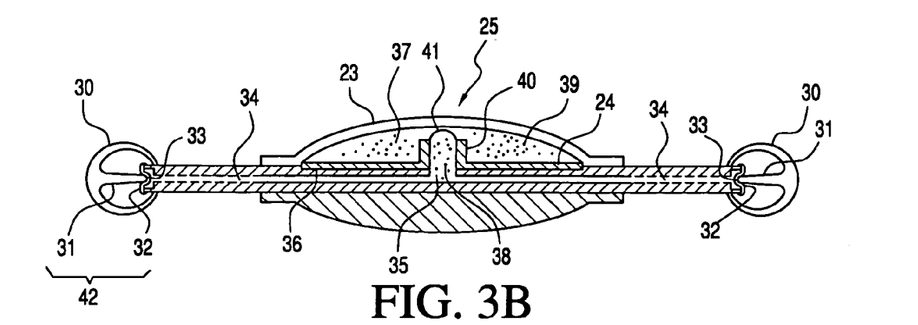

Referring to FIGS. 3A and 3B, an exemplary embodiment of an intraocular lens constructed in accordance with the principles of the present invention is described. IOL 20 comprises optic portion 21 and haptic portion 22. Optic portion 21 is constructed of light transmissive materials, while haptic portion 22 is disposed at the periphery of the optic portion and does not participate in focusing light on the retina of the eye.

Optic portion 21 comprises anterior lens element 23, actuator layer 24 including lens piston 25, substrate 26 and posterior lens element 27, all made of light-transmissive materials, such as silicone or acrylic polymers or other biocompatible materials as are known in the art of intraocular lenses. Haptic portion 22 illustratively comprises arms 28 and 29 extending from substrate 26, although other haptic configurations may be employed. Each of arms 28 and 29 terminates in transducer 30. Transducers 30 preferably each comprise a haptic piston including force-concentrating fin 31, diaphragm 32 and reservoir 33. Reservoirs 33 are coupled in fluid communication with the interior of lens piston 25 via channels 34 that extend from the reservoirs to well 35 disposed beneath lens piston 25.

In FIG. 3B, transducers 30 are in an undeformed state in which force-concentrating fins 31 apply a maximum deflection to diaphragms 32, thereby fully deflecting end wall 41 and driving anterior element 23 to the fully accommodated position. This corresponds to a fully-contracted state of the ciliary muscles, as described herein below.

Actuator layer 24 is disposed in recess 36 of substrate 26, and preferably comprises a sturdy elastomeric material. Actuator layer 24 isolates the fluid in channels 34, well 35 and the interior of lens piston 25 from the fluid disposed in the space 37 between anterior lens element 23 and actuator layer 24. Fluids 38 and 39 disposed, respectively, within channels 34 and space 37, preferably comprise silicone or acrylic oils and are selected to have refractive indices that match the materials of anterior lens element 23, actuator layer 24 and substrate 26.

In a preferred embodiment, lens piston 25 includes substantially nondeformable cylindrical side wall 40 coupled to expandable end wall 41. End wall 41 is configured to deflect outward responsive to pressure applied within sidewall 40 by fluid movement from the haptic portion. End wall 41 contacts the interior surface of anterior lens element 23, so that deflection of end wall 41 of the lens piston causes a corresponding deflection of anterior lens surface 23. Such deflections cause the anterior lens element to assume a spherical shape with a shorter radius of curvature, thereby changing the diopter power of the lens. As will of course be understood, optic portion could instead be arranged so that the lens piston deflects posterior lens element 27; the arrangement depicted in FIG. 3 is illustrative only.

The inner surface and thickness of anterior element 23 (relative to the optical axis of the lens) are selected so that the outer surface of anterior element 23 retains an optically corrective shape, e.g., spherical, throughout the entire range of motion of lens piston 25, e.g., for accommodations 0-10 diopters. It should of course be understood that the inner surface and thickness of anterior element 23 may be selected to provide an aspherical outer surface, as required for a desired degree of optical correction.

Figure 4:
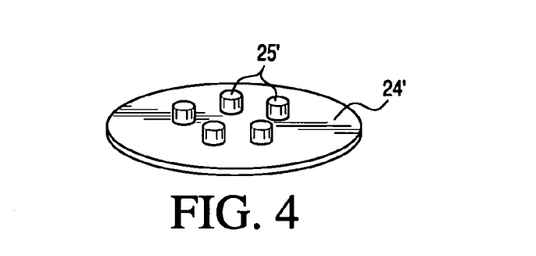
FIG. 4 is a perspective view of an alternative embodiment of lens pistons suitable for use in the intraocular lens of FIG. 3.

As shown in FIG. 3, one preferred embodiment of actuator layer 24 includes a single lens piston 25 located at the center of optic portion 21. Alternative embodiments of actuator layer 24' may include an array of lens pistons 25' spaced apart in a predetermined configuration on the anterior surface of the actuator layer, as depicted in FIG. 4, as may be required to impose a desired pattern of localized deflection on the anterior lens element. As will be apparent to one of skill in the art, an annular structure may be substituted for the individual lens pistons depicted in FIG. 4, and side walls 40 may be of any desired shape other than cylindrical.

Figure 5A:
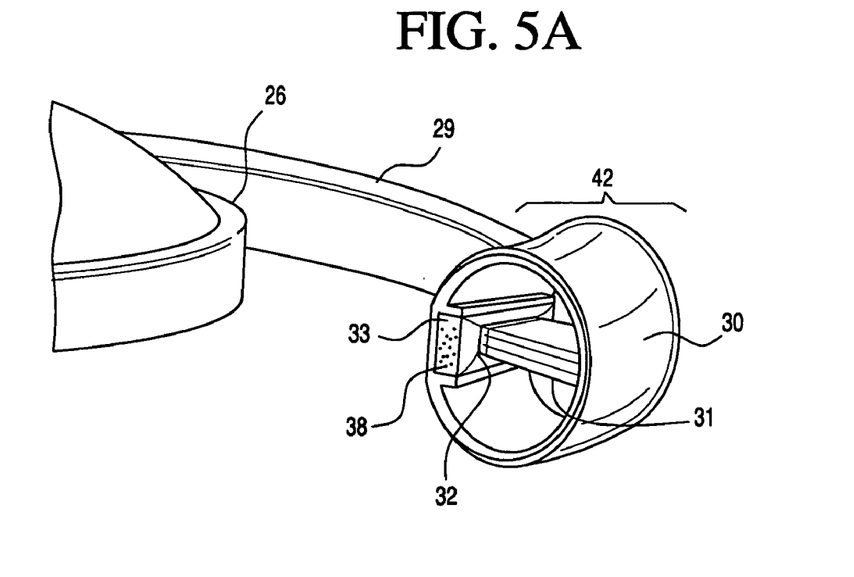
FIGS. 5A and 5B are, respectively, side sectional views of the haptic portion of the lens of FIG. 3 in the accommodated and unaccommodated states.
Figure 5B:
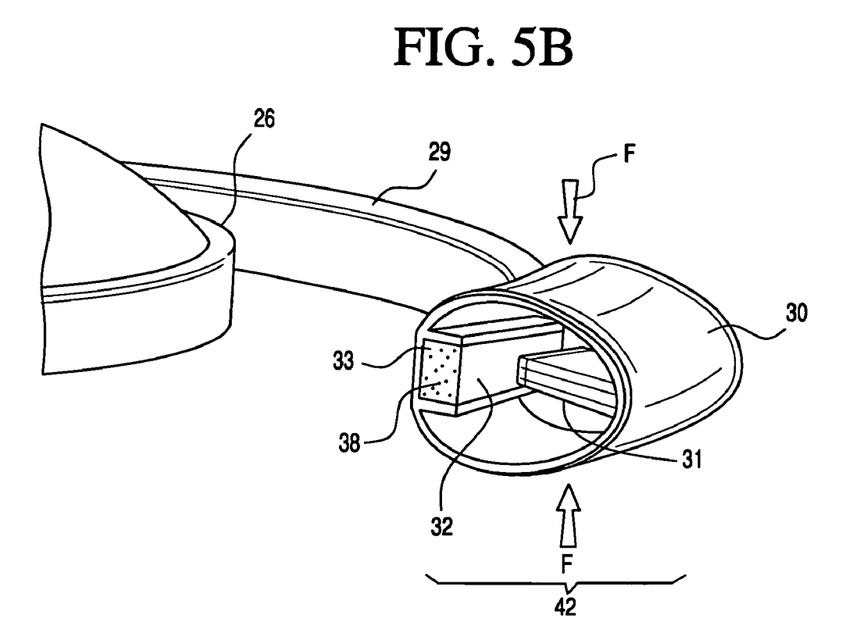

Referring now to FIGS. 5A and 5B, haptic pistons 42, constructed in accordance with the principles of the present invention are described in greater detail. Haptic pistons 40 comprise flexible and resilient transducers 30 that support force-concentrating fins 31 biased against diaphragms 32. Each diaphragm 32 comprises an elastomeric cover for a corresponding reservoir 33 filled with fluid 38. As described herein above, fluid 38 communicates through channels 34 into well 35 and the interior of lens piston 25. Transducers 30 are constructed from a resilient, elastomeric material that changes shape responsive to forces applied by capsule 15 from the ciliary muscles 13 and zonules 14.

In FIG. 5A, haptic piston 42 is shown in an undeformed state (as in FIG. 3B), corresponding to the ciliary muscles being fully contracted. In this state, the apex of fin 31 bears against diaphragm 32 to develop the maximum force resulting from the bias of transducer 30. Inward displacement of diaphragm 32 in turn displaces fluid through channels 34 (see FIG. 3) to well 35, resulting in expansion of end wall 41 of lens piston 25. When transducer 30 is in the undeformed state, fin 31 displaces the maximum volume of fluid from the haptic portion to lens piston 25, resulting in the maximum deflection of anterior element 23, and thus the maximum degree of accommodation of the lens. This corresponds to the state in which the ciliary muscles are fully contracted, and zonules 14 and capsule 15 apply the least amount of compressive force to the anterior and posterior surfaces of transducer 30.

When the ciliary muscles relax, however, the tension in the zonules increases, causing capsule 15 to assume an ellipsoidal shape (see FIG. 2A) and the lens to transition to its unaccommodated state. When the capsule becomes taut, it applies compressive forces F to the anterior and posterior surfaces of transducer 30, causing the transducer to deform to the elliptical shape depicted in FIG. 5B. Deformation of transducers 30 moves fins 31 away from diaphragms 32, thereby unloading the diaphragms and reducing the fluid pressure applied to lens piston 25. This in turn permits lens piston 25 to move to an undeflected state, reducing deflection of anterior lens element 23 and returning the lens to an unaccommodated state.

Figure 6A:
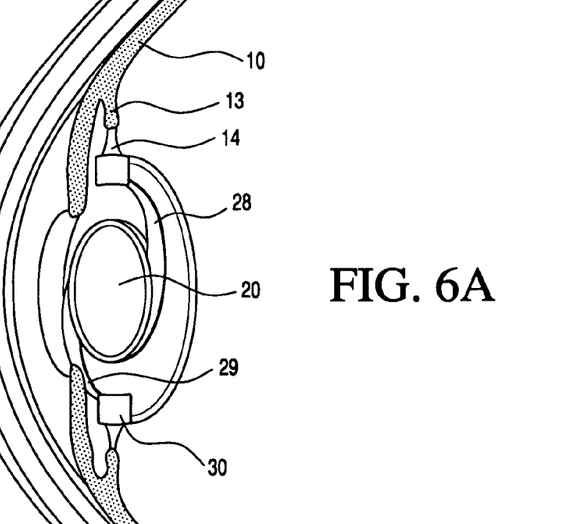
FIGS. 6A-6C are, respectively, a perspective view of the lens of FIG. 3 disposed in a human eye and side sectional views of the lens in the accommodated and unaccommodated states.
Figure 6B:
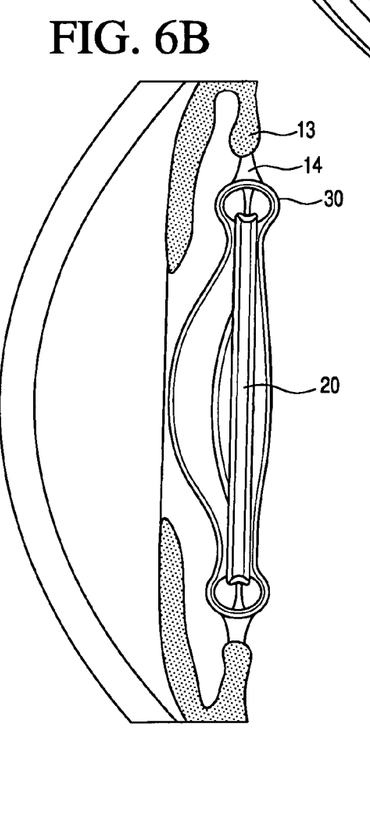
Figure 6C:
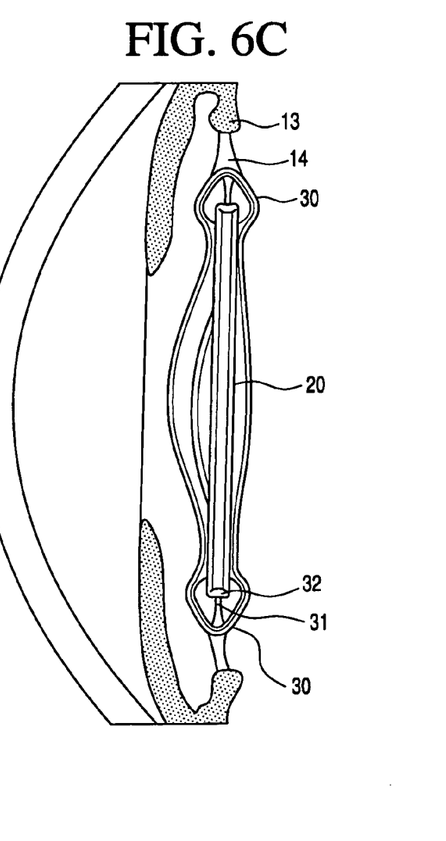

Referring now to FIGS. 6A to 6C, IOL 20 is shown implanted into capsule 15 of human eye 10. When so implanted, haptic arms 28 and 29 support the IOL within the capsule, while transducers 30 engage the interior of the capsule at locations adjacent to ciliary muscles 13. In FIG. 6B the ciliary muscles are shown in a contracted state, in which the compressive forces applied by zonules 14 and capsule 15 to transducers 30 is lowest and transducers 30 assume the undeformed position. This also corresponds to transducers 30 applying the least tension to capsule 15 and zonules 14. As discussed above, in the undeformed position, fins 30 are biased against diaphragms 32, displacing fluid 38 from reservoirs 33 to the lens piston. In FIG. 6C, the ciliary muscles are relaxed, and zonules 14 pull capsule 15 taut into an ellipsoidal shape. As noted above, in this state the capsule applies compressive forces to the lateral surfaces of transducers 30 that ensure that lens piston 25 is drawn to its fully retracted position.

In accordance with one aspect of the present invention, the volume of fluid in the accommodating lens may be selected so that the forces required to provide a useable range of accommodation are satisfactory for a preselected population of patients. Alternatively, the volume of fluid used in IOL 20 may be specified during manufacture for a given patient, or may be adjusted prior to implantation of the IOL on a patient-by-patient basis. In this manner, the forces developed by lens piston 25 and haptic pistons 42 may be tailored for a specific patient. In addition, the number, shape and placement of lens pistons 25' on actuator layer 24' may be selected, e.g., prescribed during manufacture, to optimize accommodation of the lens for a specific patient.

It may been noted that in the undeformed state, transducers 30 maintain the lens in the accommodated or high power state. Accordingly, any failure that allows the transducers to assume the undeformed state without any physiologic influence could result in a residual near-sighted condition. In accordance with another aspect of the present invention it would be advantageous to provide for a mechanism to relieve a small amount of quiescent pressure within the lens so that the lens piston assumes the unaccommodated, low power state.

To accomplish this result, a relief valve in the form of a sacrificial plug may de disposed on a channel that leads to an evacuated cavity. The plug may be constructed of material that remodels when activated by a laser to permit a reduction of the pressure in the lens piston, and thereby allowing the anterior lens element to assume the unaccommodated state. The plug preferably comprises a colored material that readily and preferentially absorbs laser light, for example, 1.06 micron wavelength radiation from a Nd:YAG laser. When irradiated, the plug experiences a phase change or otherwise deforms to permit a predetermined quantity of fluid in the channel 34 to enter the evacuated cavity.

Figure 7A:
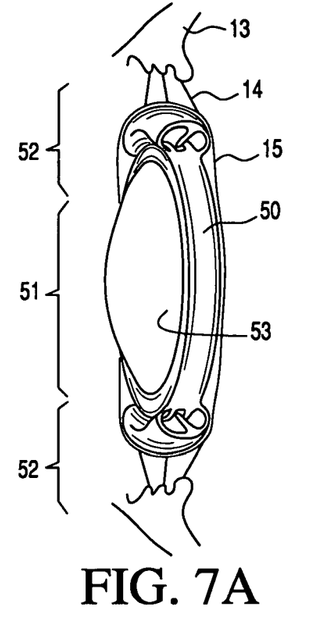
FIGS. 7A-7C are, respectively, a perspective view and side sectional views in the accommodated and unaccommodated states of an embodiment of the intraocular lens of the present invention that is directly actuated by ciliary muscle.
Figure 7B:
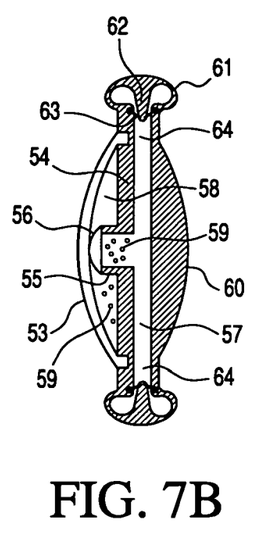
Figure 7C:
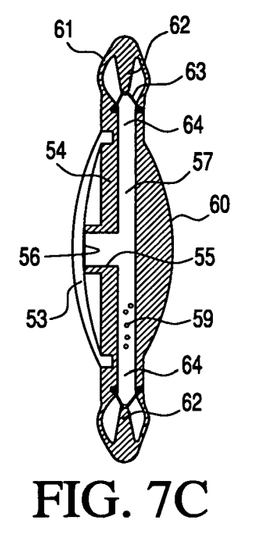

Referring now to FIGS. 7A to 7C, an alternative embodiment of the IOL of the present invention is described. IOL 50 comprises optic portion 51 and haptic portion 52. Optic portion 51 comprises anterior lens element 53 and substrate 54 formed of light-transmissive materials. Substrate 54 includes lens piston 55 having expandable end wall 56, and fluid channels 57 in fluid communication with the interior of lens piston 55. Expandable end wall 56 contacts the inner surface of anterior lens element 53, so that deflection of end wall 56 causes anterior lens element 53 to assume a more convex shape. The thickness profile of anterior lens element 53 is tailored to a desired degree of optical correction when deflected, as previously described. Channels 57 and space 58, disposed between anterior lens element 53 and substrate 54, are filled with fluid 59 having an index of refraction that is matched to the materials of anterior lens element 53 and substrate 54. Substrate 54 may include integrally formed posterior lens element 60.

Haptic portion 52 is disposed at the periphery of optic portion 51, and includes transducers 61 that include force-concentrating fins 62 coupled to diaphragms 63. Fluid channels 57 extend circumferentially along the edges of substrate 54 for an arc-length corresponding to the arc-length of haptic portions 52 to form edge recesses 64 that function as reservoirs. Transducer 61, fin 62, diaphragm 63 and edge recess 64 together form a haptic piston that adjusts the deflection of end wall 56 of lens piston 55 responsive to contraction and relaxation of the ciliary muscle, zonules and capsule.

As in the embodiment of FIGS. 3-6, transducers 61 are constructed so that, in the undeformed state, they bias force-concentrating fins 62 to cause the maximum inward displacement of diaphragms 63. Because diaphragms 63 of the haptic pistons are coupled to fins 62, compressive forces applied to the anterior and posterior faces of transducers 61 by the capsule during relaxation of the ciliary muscles urges the IOL to its unaccommodated state by deforming transducers 61 and withdrawing fluid from lens piston 55.

As illustrated in FIG. 7B, contraction of the ciliary muscles causes the zonules and capsule to relax, thereby reducing the compressive forces applied by the capsule to transducers 61. This permits transducers 61 to return to an undeformed state in which fins 62 extend radially inward to displace diaphragms 63 into edge recesses 64. This in turn displaces fluid 59 to the lens piston, causing end wall 56 to deflect anterior lens element 53 to the accommodated state.

Relaxation of the ciliary muscles causes the zonules and capsule to become taut, thereby compressing transducers 61 to deform to the position shown in FIG. 7C. More specifically, the compressive forces applied by the zonules and capsule deform transducers 61 to an elongated shape. This in turn causes fins 62 and diaphragms 63 to deflect outward away from edge recesses 64, and draw fluid from lens piston 55, returning the lens to its unaccommodated state.

Figure 8A:
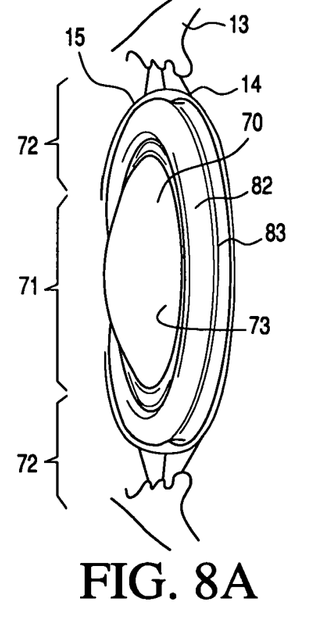
FIGS. 8A-8C are, respectively, a perspective view and side sectional views in the accommodated and unaccommodated states of a further alternative embodiment of the intraocular lens of the present invention.
Figure 8B:
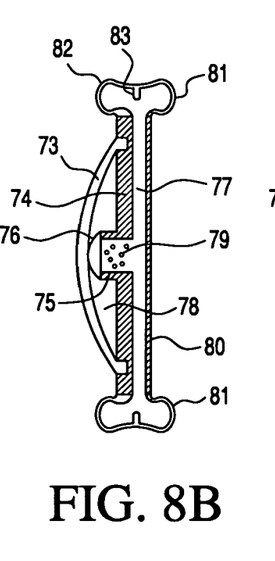
Figure 8C:
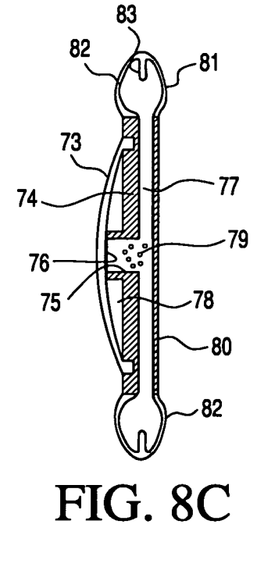

Referring to FIGS. 8A-8C, another alternative embodiment of the intraocular lens of the present invention is described. IOL 70 includes optic portion 71 and haptic portion 72. IOL 70 differs from the IOL 50 primarily in that haptic portion 72 is disposed around the entire optic portion, and in addition haptic portion 72 omits the use of haptic pistons, as in the preceding embodiments.

Optic portion 71 comprises anterior lens element 73 and substrate 74 formed of light-transmissive materials. Substrate 74 includes lens piston 75 having expandable end wall 76, and fluid channels 77 in fluid communication with the interior of lens piston 75. Expandable end wall 76 contacts the inner surface of anterior lens element 73, so that deflection of end wall 76 causes anterior lens element 73 to assume a more convex shape, as in the preceding embodiments. The thickness profile of anterior lens element 73 is tailored to produce a desired degree of accommodation when deflected, as previously described. Channels 77 and space 78, disposed between anterior lens element 73 and substrate 74, are filled with fluid 79 having a matched index of refraction. Substrate 74 may define a posterior lens surface 80, or may include a separate lens element.

Haptic portion 72 is disposed surrounding the periphery of optic portion 71, and includes transducer 81. Transducer 81 comprises diaphragm 82 including elastomeric ring 83 disposed along the midline of the diaphragm that biases the ring to the radially compressed state depicted in FIGS. 8A and 8B. This state corresponds to the maximum deflection of lens piston 75, and thus the state of maximum accommodation of lens 70. Ring 83 also ensures that diaphragm 82 engages and applies tension to the capsule. Transducer 81 adjusts the deflection of end wall 76 of lens piston 75 responsive to contraction and relaxation of the ciliary muscle, zonules and capsule.

More specifically, contraction of the ciliary muscles causes the zonules and capsule to relax, thereby reducing the compressive forces applied by the capsule to transducer 81. This permits the transducer to return to an undeformed state, in which ring 83 biases diaphragm 82 to displace fluid to lens piston 75. This in turn causes end wall 76 to deflect anterior lens element 73 to the accommodated state.

Relaxation of the ciliary muscles causes the zonules and capsule to become taut, thereby applying compression to the anterior and posterior surfaces of transducer 81 to deform to the diaphragm to the position shown in FIG. 8C. In particular, the compressive forces applied by the zonules and capsule deform transducer 81 to an elongated shape that reduces the pressure on fluid 59 and permits end wall 76 of lens piston 75 to transition to the undeflected state shown in FIG. 8C. This in turn reduces deflection of anterior lens element 73 and returns the lens to its unaccommodated state.

Figure 9A:
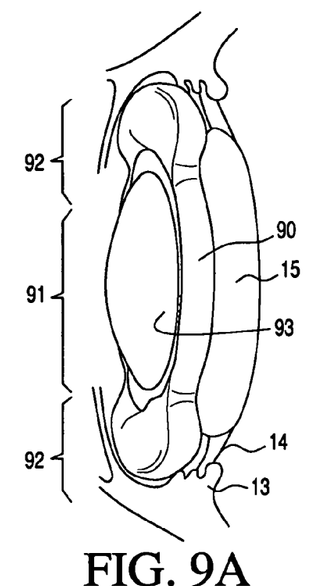
FIGS. 9A-9C are, respectively, a perspective view and side sectional views in the accommodated and unaccommodated states of another alternative embodiment of the intraocular lens of the present invention.
Figure 9B:
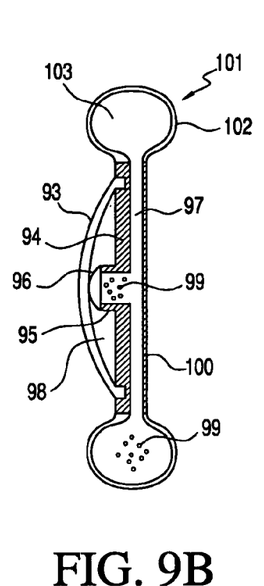
Figure 9C:
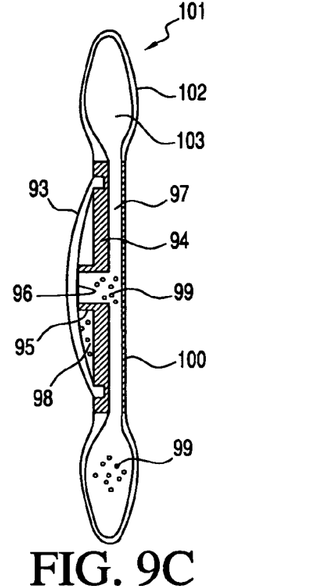

Referring now to FIGS. 9A-9C, a second family of embodiments of intraocular lenses is described. Unlike the preceding embodiments, in which action of the ciliary muscle is transmitted to the IOL via the zonules and capsule, in this embodiment action of the ciliary muscle directly against the transducer is communicated to the lens piston. As depicted in FIG. 9A, IOL 90 may be implanted anterior to the capsule, and includes optic portion 91 and haptic portion 92.

Optic portion 91 comprises anterior lens element 93 and substrate 94 formed of light-transmissive materials. Substrate 94 includes lens piston 95 having expandable end wall 96, and fluid channels 97 in fluid communication with the interior of lens piston 95. Expandable end wall 96 contacts the inner surface of anterior lens element 93, so that deflection of end wall 96 causes anterior lens element 93 to assume a more convex shape. As in the preceding embodiments, the thickness profile of anterior lens element 93 may be tailored to produce a desired degree of accommodation when deflected. Channels 97 and space 98, disposed between anterior lens element 93 and substrate 94, are filled with fluid 99 having a matched index of refraction. Substrate 94 may define a posterior lens surface 100, or may include a separate lens element.

The optical power provided by posterior lens surface 100 may be used to provide the base power of the device, and may be tailored for specific patient population. The profile of posterior lens surface 100 also may be chosen to provide optimal performance of the optical system in concert with the optical correction provided by anterior lens element 93 throughout its range of motion.

In addition or alternatively, any error of the refractive surface of anterior lens element 93, for example 1 or 2 microns or less of wave error that the surface experiences throughout its range of motion, may be further reduced by adding a small compensating thickness to anterior lens element 93, in exactly the reverse sense of the error, e.g., corresponding to the average error incurred at each point on anterior lens element 93 through its range of motion.

Haptic portion 92 includes a plurality of transducers 101, each transducer comprising diaphragm 102. Transducers 101 are designed to directly engage the ciliary muscle in the area of the sulcus, and comprise resilient, flexible diaphragms 102 that have an undeformed shape depicted in FIG. 9C. The interiors of diaphragms 102 form reservoirs 103 communicate with channels 97, and are filled with index-matched fluid 99.

Contraction of the ciliary muscles applies a radially compressive force to the transducers that transitions the diaphragms to the shape depicted in FIG. 9B. This causes fluid to be displaced from reservoirs 103 of transducers 101, pressurizing the fluid in channels 99 and lens piston 95. Responsive to this pressure increase, end wall 96 of the lens piston expands anteriorly, deflecting anterior lens element 93 and transitioning the lens to the accommodated state, as shown in FIG. 9B.

When the ciliary muscle subsequently relaxes, the radially compressive forces applied by the muscles diminish, transducer 101 returns to an undeformed state of FIG. 9C, and lens piston resumes its unexpandable position. This in turn reduces deflection of anterior lens element 93 and returns the lens to its unaccommodated state.

While the design of the haptic portion of the embodiment of FIG. 9 is similar to those of previously-known fluid-mediated accommodating intraocular lenses, such as those described in the aforementioned patent to Christie, the presence of lens piston 95 is expected to provide significantly greater volumetric mechanical advantage and greater dynamic range than could be achieved with prior art designs.

Whereas previously-known designs distribute a pressure increase resulting from action of the ciliary muscle over the entire surface of the lens, the lens piston of the present invention amplifies motion of the ciliary muscle, e.g., 100 microns, by the ratio of the transducer area to the area of the lens piston. It is expected that ratios of 2 or more may be readily achieved, however, a ratio of one may be sufficient for many patient populations. Accordingly, the amount of fluid that must be displaced to optically correct axial displacement of the refractive surface of anterior lens element 23 is relatively small.

Figure 10A:
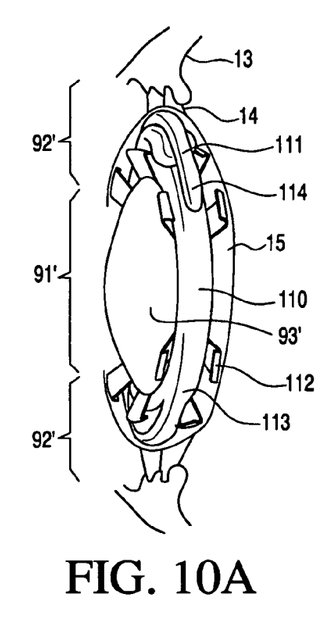
FIGS. 10A-10C are, respectively, a perspective view and side sectional views in the accommodated and unaccommodated states of a further embodiment of the intraocular lens of the present invention.
Figure 10B:
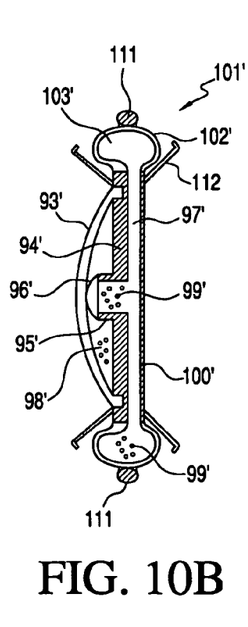
Figure 10C:
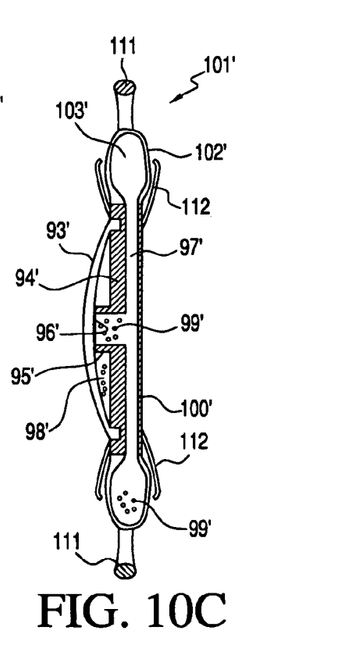

With respect to FIGS. 10A-10C, a third family of embodiments of the intraocular lens of the present invention is described. Like the embodiments of FIGS. 3-8, IOL 110 is implanted within the capsule, includes haptic pistons, and is actuated by action of the ciliary muscles, zonules and capsule. However, as in the embodiment of FIG. 9, the lens is unaccommodated in its unstressed condition, and transitions to the accommodated state upon application of radially compressive forces. In particular, whereas the embodiments of FIGS. 3-6 transition from the accommodated state to the unaccommodated state by virtue of lateral (anterior and posterior) compressive forces applied during the capsule during relaxation, the embodiment of FIG. 10 transitions to the accommodated state upon thickening of the capsular equator during contraction of the ciliary muscles.

The structure of IOL 110 is similar to that of IOL 90 of FIG. 9, with like parts identified by like-primed numbers, except that transducers 101' are surrounded by force concentrating elements 111, and haptic portions 92' further comprise flanges 112 that orient IOL 110 within the capsule and maintain tension on the zonules.

More specifically, IOL 110 includes optic portion 91' and haptic portion 92'. Optic portion 91' comprises anterior lens element 93' and substrate 94' formed of light-transmissive materials. Substrate 94' includes lens piston 95' having expandable end wall 96', and fluid channels 97' in fluid communication with the interior of lens piston 95'. Expandable end wall 96' contacts the inner surface of anterior lens element 93', so that deflection of end wall 96' causes anterior lens element 93' to assume a more convex shape. As in the preceding embodiments, the thickness profile of anterior lens element 93' may be tailored to produce a desired degree of accommodation when deflected. Channels 97' and space 98', disposed between anterior lens element 93' and substrate 94', are filled with fluid 99' having a matched index of refraction. Substrate 94' defines posterior lens surface 100'.

Haptic portion 92' includes transducers 101', with each transducer having diaphragm 102'. Arcuate force-concentrating elements 111 are disposed radially outward of transducers 101' and illustratively have fixed end 113 connected to haptic portion 92 and free end 114. Elements 111 contact the equator of capsule 15 and flex radially inward or outward to follow thickening or thinning of the capsular equator responsive to contraction of the ciliary muscles. Elements 111, diaphragms 102', and reservoirs 103' together form haptic pistons. Elements 111 and diaphragms 102' have an undeformed shape depicted in FIG. 10C. As in the preceding embodiments reservoirs 103' communicate with channels 97', and are filled with index-matched fluid 99'. As noted above, laterally-extending flanges 112 apply tension to the capsule to orient the IOL within the capsule and maintain tension on the zonules when the capsule changes shape responsive to action of the ciliary muscles.

As described herein above with respect to FIG. 2, contraction of the ciliary muscles causes the capsule to become more spherical and thicken along its equator. This thickening applies a radially compressive force to elements 111 of transducers 101' that compresses diaphragms 102' to the deformed shapes depicted in FIGS. 10A and 10B. This causes fluid to be displaced from reservoirs 103' of transducers 101', pressurizing the fluid in channels 97' and lens piston 95'. Responsive to this pressure increase, end wall 96' of the lens piston expands anteriorly, deflecting anterior lens element 93' and transitioning the lens to the accommodated state, as shown in FIG. 10B. Frames 112 retain IOL 110 centered on the capsular equator as the capsule transitions to a more spherical shape.

When the ciliary muscle subsequently relaxes, the radially compressive forces applied by the muscles diminish, the capsule becomes more ellipsoidal, and the capsular equator thins. Frames 112 become compressed by the lateral forces applied by the capsule and zonules, and transducers 101' follow the elongation of the capsule, with free ends 114 of elements 111 deflecting outward to the undeformed state depicted in FIG. 10C. This in turn relieves compression of diaphragms 102', so that fluid moves from channels 97' back to reservoirs 103', and lens piston 95' resumes its unexpanded position. Consequently, anterior lens element 93' returns to its undeflected state and lens 110 transitions to the unaccommodated state shown in FIG. 10C.

Figure 11A:
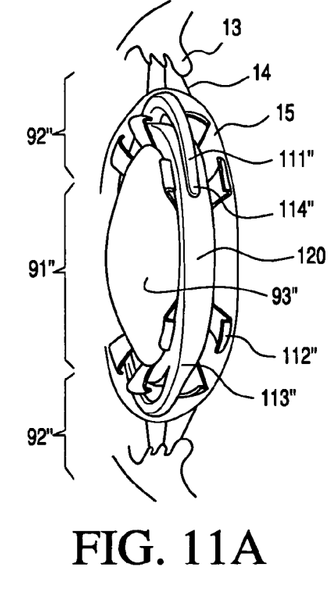
FIGS. 11A-11C are, respectively, a perspective view and side sectional views in the accommodated and unaccommodated states of still another embodiment of the intraocular lens of the present invention.
Figure 11B:
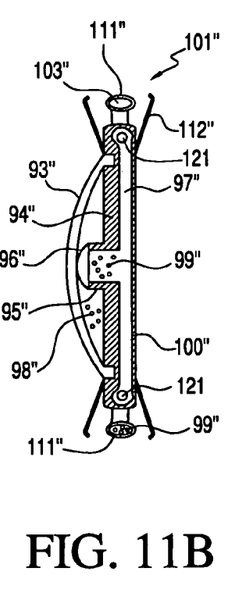
Figure 11C:
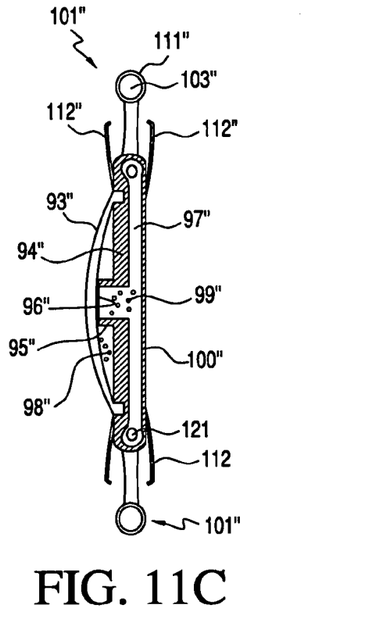

Referring to FIGS. 11A-11C, a further alternative embodiment of the intraocular lens of the present invention is described. IOL 120 is similar in construction to IOL 110, and like components are designated by like double prime numbers. Thus, for example, while the anterior lens element of FIG. 10A is designated 93', the anterior lens element of FIG. 11A is designated 93". IOL 120 differs from IOL 110 of FIG. 10 in that diaphragm 102' is omitted, and reservoir 103" is defined by an internal lumen of element 111" that communicates with channel 97" via opening 121. In IOL 120, element 111" therefore defines transducer 101".

As in IOL 110 of FIG. 10, IOL 120 is disposed within the capsule and transitions to the accommodated state upon thickening of the capsular equator during contraction of the ciliary muscles. Flanges 112" that orient the IOL within the capsule and maintain tension on the zonules.

IOL 120 includes optic portion 91" and haptic portion 92". Optic portion 91" comprises anterior lens element 93" and substrate 94" formed of light-transmissive materials. Substrate 94" includes lens piston 95" having expandable end wall 96", and fluid channels 97" in fluid communication with the interior of lens piston 95". Expandable end wall 96" contacts the inner surface of anterior lens element 93", so that deflection of end wall 96" causes anterior lens element 93" to assume a more convex shape. As in the preceding embodiments, the thickness profile of anterior lens element 93" may be tailored to produce a desired degree of accommodation when deflected. Channels 97" and space 98", disposed between anterior lens element 93" and substrate 94", are filled with index-matched fluid 99". Substrate 94" defines posterior lens surface 100".

Haptic portion 92" includes transducers 101" in the form of arcuate elements 111" having fixed end 113" connected to haptic portion 92" and free end 114". Elements 111" include internal lumens defining reservoirs 103" that are in fluid communication with channels 97" via openings 121. Elements 111" contact the equator of capsule 15 and flex radially inward or outward to follow thickening or thinning of the capsular equator responsive to contraction of the ciliary muscles. Elements 111" have the undeformed shape depicted in FIG. 11C. Reservoirs 103"m, channels 97" and lens piston 95" are filled with index-matched fluid 99". As noted above, laterally-extending flanges 112" apply tension to the capsule to orient the IOL within the capsule and maintain tension on the zonules when the capsule changes shape responsive to action of the ciliary muscles.

As for IOL 110, contraction of the ciliary muscles causes the capsule to become more spherical and thicken along its equator, thereby applying a radially compressive force to transducers 101" that compresses elements 111" to the deformed flatter (smaller volume) shapes depicted in FIGS. 11A and 11B. This causes fluid to be displaced from reservoirs 103" of transducers 101", pressurizing the fluid in channels 97" and lens piston 95". Responsive to this pressure increase, end wall 96" of the lens piston expands anteriorly, deflecting anterior lens element 93" and transitioning the lens to the accommodated state, as shown in FIG. 11B. Frames 112" retain IOL 120 centered on the capsular equator as the capsule transitions to a more spherical shape.

When the ciliary muscle subsequently relaxes, the radially compressive forces applied by the muscles diminish, the capsule becomes more ellipsoidal, and the capsular equator thins. Frames 112" become compressed by the lateral forces applied by the capsule and zonules, and transducers 101" follow the elongation of the capsule, with free ends 114" of elements 111" deflecting outward to the undeformed rounder (larger volume) state depicted in FIG. 11C. This in turn relieves compression of transducers 101", so that fluid moves from channels 97" back to reservoirs 103", and lens piston 95" resumes its unexpanded position. Consequently, anterior lens element 93" returns to its undeflected state and lens 120 transitions to the unaccommodated state shown in FIG. 11C.

Figure 12A:
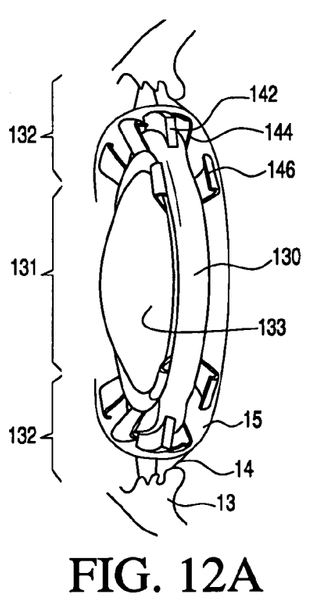
FIGS. 12A-12C are, respectively, a perspective view and side sectional views in the accommodated and unaccommodated states of yet another embodiment of the intraocular lens of the present invention.
Figure 12B:
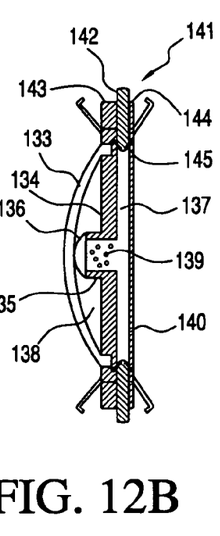
Figure 12C:
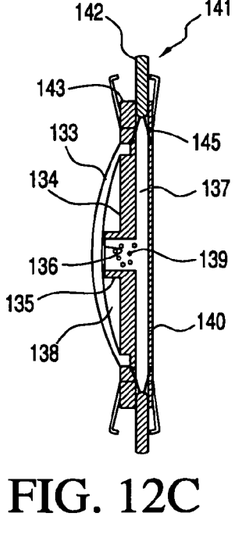

In FIGS. 12A-12C, still another embodiment of an intraocular lens constructed in accordance with the principles of the present invention is described. IOL 130 comprises optic portion 131 and haptic portion 132. Optic portion 131 comprises anterior lens element 133 and substrate 134 formed of light-transmissive materials. Substrate 134 includes lens piston 135 having expandable end wall 136, and fluid channels 137 in fluid communication with the interior of lens piston 135.

Expandable end wall 136 contacts the inner surface of anterior lens element 133, so that deflection of end wall 136 causes anterior lens element 133 to assume a more convex shape. The thickness profile of anterior lens element 133 is tailored to provide a desired degree of optical correction throughout its range of deflection. Channels 137 and space 138, disposed between anterior lens element 133 and substrate 134, are filled with fluid 139 having an index of refraction that is matched to the materials of anterior lens element 133 and substrate 134. Substrate 134 includes posterior lens surface 140.

Haptic portion 132 is disposed at the periphery of optic portion 131, and includes transducers 141 having segments 142 slidably disposed in edge recesses 143. Edge recesses 143 are defined by extensions 144 of fluid channels 137 that extend circumferentially along the edges of substrate 134 for an arc-length corresponding to the arc-length of haptic portions 132 and function as reservoirs. Segments 142 are coupled to diaphragms 145 so that force applied to the outer edges of segments 142 by the capsular equator causes the segments to be displaced radially inward. Laterally-extending flanges 146 apply tension to the capsule to orient IOL 130 within the capsule and maintain tension on the zonules.

Segment 142, substrate extensions 144, diaphragm 145 and edge recess 143 together form a haptic piston that transfers fluid to lens piston 135 responsive to contraction and relaxation of the ciliary muscle, zonules and capsule. Specifically, inward movement of segments 142 causes diaphragms 145 to displace inwardly into edge recesses 143, thereby transferring fluid to lens piston 135. As in the preceding embodiment, fluid entering lens piston 135 expands end wall 136, thereby deflecting anterior lens element 133 to its accommodated shape, as shown in FIGS. 12A and 12B.

In FIG. 12C, when the ciliary muscles relax, the capsule elongates and applies laterally compressive forces to flanges 146. As the capsule elongates, the forces applied to segments 142 decrease, allowing end wall 136 to return to its unexpanded state and permitting anterior lens element 133 to return to the unaccommodated state.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An intraocular lens configured for implantation in a capsule following extraction of a lens, the intraocular lens being configured and adapted to accommodate in response to contraction of a patient's ciliary muscles, the intraocular lens comprising:
   a substrate having a portion defining a fluid channel;
   a lens element;

an actuator layer interposed between the lens element and the substrate, the actuator layer having at least one lens piston disposed in contact with the lens element, the lens piston coupled in fluid communication with the fluid channel;

a haptic portion having a reservoir coupled in fluid communication with the fluid channel; and a fluid disposed in the lens piston, fluid channel and reservoir, wherein a transfer of fluid from the reservoir to the lens piston to deflect the lens element is induced in response to movement of the patient's ciliary muscles.

2. The intraocular lens of claim 1 wherein the lens piston is disposed in the center of the actuating layer.

3. The intraocular lens of claim 1 wherein the lens element has a non-uniform radial thickness selected to maintain a desired degree of optical correction throughout a range of deflection of the lens element.

4. The intraocular lens of claim 1 wherein the fluid has a refractive index substantially the same as a refractive index of the lens element, substrate and actuator layer.

5. The intraocular lens of claim 4 wherein the haptic portion comprises at least one haptic piston.

6. The intraocular lens of claim 5 wherein the haptic piston comprises:
a diaphragm disposed in contact with the fluid to define a flexible boundary of the reservoir; and
a force-concentrating element operatively associated with the diaphragm configured and adapted to communicate forces from the ciliary muscles to the diaphragm.

7. The intraocular lens of claim 6 wherein the force concentrating element is disposed in contact with the diaphragm.

8. The intraocular lens of claim 6 wherein the force concentrating element is coupled to the diaphragm.

9. The intraocular lens of claim 8 wherein the force concentrating element comprises a segment slidably disposed in an extension of the substrate.

10. The intraocular lens of claim 1 wherein the haptic portion further comprises one or more flanges that are configured and adapted to apply tension to the capsule.

11. The intraocular lens of claim 1 wherein the haptic portion comprises two or more arms extending from the substrate.

12. An intraocular lens comprising:
an optic portion having a lens element;
a haptic portion coupled to the optic portion;
an actuator layer disposed in the optic portion, the actuator layer including a lens piston;
a reservoir disposed in the haptic portion, the reservoir in fluid communication with lens piston;
a fluid disposed in the lens piston and reservoir,
wherein forces applied to the haptic portion move fluid between the reservoir and the lens piston to control expansion of the lens piston, expansion of the lens piston deflecting the lens element.

13. The intraocular lens of claim 12 wherein the optic portion comprises optically transparent materials.

14. The intraocular lens of claim 12 wherein the lens element has a thickness selected to maintain a desired degree of optical correction throughout a range of deflection of the lens element.

15. The intraocular lens of claim 12 further comprising a substrate including a portion defining a fluid channel that couples the haptic portion to the lens piston.

16. The intraocular lens of claim 12 wherein the lens element is an anterior lens element and the optic portion further comprises a posterior lens element.

17. The intraocular lens of claim 16 wherein the posterior lens element is integrally formed with the substrate.

18. The intraocular lens of claim 12 wherein the fluid has a refractive index substantially the same as a refractive index of the lens element and actuator layer.

19. The intraocular lens of claim 12 wherein the haptic portion comprises at least one haptic piston.

20. The intraocular lens of claim 19 wherein the haptic piston comprises:
a diaphragm disposed in contact with the fluid to define a flexible boundary of the reservoir; and
a force-concentrating element operatively associated with the diaphragm configured and adapted to communicate forces from the ciliary muscles to the diaphragm.

21. The intraocular lens of claim 20 wherein the force concentrating element is disposed in contact with the diaphragm.

22. The intraocular lens of claim 20 wherein the force concentrating element is coupled to the diaphragm.

23. The intraocular lens of claim 22 wherein the force concentrating element comprises a segment slidably disposed in an extension of the substrate.

24. The intraocular lens of claim 12 wherein the haptic portion further comprises one or more flanges that are configured and adapted to apply tension to the capsule.

25. The intraocular lens of claim 12 wherein the haptic portion comprises two or more arms extending from the substrate.

26. The intraocular lens of claim 12 further comprising a valve that transitions the intraocular lens to an unaccommodated state.

27. The intraocular lens of claim 1 further comprising a valve that transitions the intraocular lens to an unaccommodated state.

* * * * *